United States Patent
Qing et al.

(10) Patent No.: US 8,707,213 B2
(45) Date of Patent: Apr. 22, 2014

(54) METHODS AND SYSTEMS FOR IMPLEMENTING HOT KEYS FOR OPERATING A MEDICAL DEVICE

(75) Inventors: Lei Qing, Shenzhen (CN); Dazhi Teng, Shenzhen (CN); Lingbo Zeng, Shenzhen (CN); Xu Luo, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 342 days.

(21) Appl. No.: 12/886,371

(22) Filed: Sep. 20, 2010

(65) Prior Publication Data

US 2011/0072384 A1 Mar. 24, 2011

(30) Foreign Application Priority Data

Sep. 21, 2009 (CN) .......................... 2009 1 0190463

(51) Int. Cl.
*G06F 3/048* (2013.01)
(52) U.S. Cl.
USPC ........... 715/847; 715/745; 715/747; 715/811; 715/812
(58) Field of Classification Search
USPC ......................... 715/847, 745, 747, 811, 812
See application file for complete search history.

(56) References Cited

U.S. PATENT DOCUMENTS

| | | |
|---|---|---|
| 2004/0109028 A1 | 6/2004 | Stern et al. |
| 2005/0015728 A1* | 1/2005 | Ragan et al. ................. 715/765 |
| 2006/0218506 A1* | 9/2006 | Srenger et al. ............... 715/810 |
| 2007/0180407 A1* | 8/2007 | Vahtola ........................ 715/847 |
| 2010/0050128 A1* | 2/2010 | Chiang et al. ................ 715/847 |

FOREIGN PATENT DOCUMENTS

| | | |
|---|---|---|
| CN | 101042612 A | 9/2007 |
| CN | 101234027 A | 8/2008 |
| CN | 101452691 A | 6/2009 |
| DE | 3504578 A1 | 8/1986 |
| DE | 3513862 A1 | 10/1986 |
| JP | 6154172 A | 6/1994 |

OTHER PUBLICATIONS

Zheng, Qingsheng, "Function Key Programing Technology of X Ray CT Machine," CT Rom Anqing Hospital Anhui.
Guo, Jinghai, "Development of X-Ray Diagnostic Imaging Information System," Medical Beauty Center of China People's Liberation Army.

* cited by examiner

*Primary Examiner* — Amy Ng
*Assistant Examiner* — Claudia Dragoescu
(74) *Attorney, Agent, or Firm* — Kory D. Christensen; Stoel Rives LLP

(57) ABSTRACT

Methods and systems for implementing hot keys for operating a medical instrument are disclosed. The hot keys may be implemented by: receiving a user input selecting a function from a menu, tracking a frequency with which each function is selected from the menu, associating the hot keys with functions according to the frequency with which each function is selected from the menu, and displaying the hot keys in the hot key display area on a display device of the medical instrument.

12 Claims, 4 Drawing Sheets

METHODS AND SYSTEMS FOR IMPLEMENTING HOT KEYS FOR OPERATING A MEDICAL DEVICE

CROSS-REFERENCE TO RELATED APPLICATIONS

This application claims priority to Chinese Patent Application No. 200910190463.8, filed Sep. 21, 2009, which is incorporated herein by reference in its entirety.

TECHNICAL FIELD

This disclosure relates to user interfaces for medical devices.

SUMMARY

Methods and systems for implementing hot keys for operating a medical device are disclosed.

DETAILED DESCRIPTION

Currently, electronic products are being made with an increasing number of functions, such that operating the electronic products is becoming increasingly complicated. User interfaces for many functions are set in deep multi-level menu structures, and the functions can only be selected through multiple operations. Many medical instruments, such as patient monitors and ultrasonic diagnosis devices, have such characteristics. In medical institutions (e.g., emergency treatment, intensive care, and surgery), doctors and nurses concentrate on patient care, which can sometimes lead to operational errors of complicated medical instruments. Such operational errors have an adverse impact on diagnosis and treatment, and may even endanger patient lives.

On typical medical devices, hard keys are arranged on a hardware panel, or functional "hot" keys (e.g., keyboard shortcuts) are displayed on a screen interface. Unfortunately, because labels on the hard keys are fixed or cannot be easily changed, the hard keys can only implement fixed functions or operations. Likewise, hot keys displayed on the screen interface are typically pre-defined by manufacturers and cannot be altered by the user.

To address these problems, a medical instrument according to one embodiment includes an operating device, a processing device, and a display device. The operating device generates signals after being operated by the user. The processing device receives the signals, performs processing according to the signals, and sends processing results to the display device for display. In one embodiment, the display device is provided with function keys and hot keys in a portion of a display interface. The operating device is operated by the user to generate signals for defining the hot keys, and the processing device defines the hot keys according to the signals for defining the hot keys.

In one embodiment, the operating device may include keys, knobs, knobs with keys, trackballs, keyboards, mice, and/or other components. A user can operate the medical instrument through the operating device, for example, by moving the cursor or inputting information or instructions. The processing device may include a processor, storage device, and other components, for performing information processing. The display device may include a monitor for displaying information before, during, or after processing. Various function keys may be displayed on the display device. The user operates on the function keys through the operating device, so as to implement the corresponding functions.

In various embodiments, hot keys may also be displayed on the display device. The hot keys are may be displayed in a fixed area of the display device and do not change positions frequently during user operation. Therefore, some frequently used or important function keys are often defined as the hot keys. The hot keys can be defined by the user through the following methods.

Figure 1:
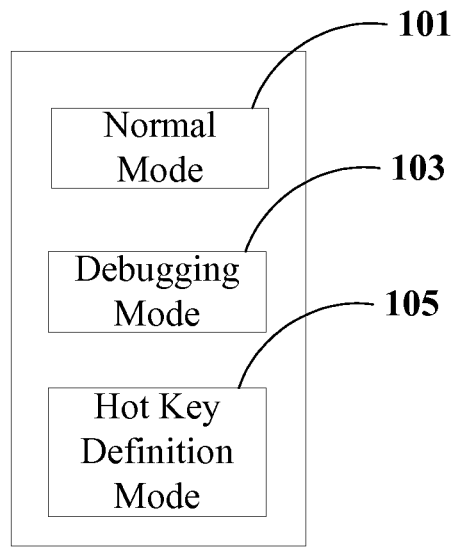
FIG. 1 is a schematic view of a mode selection menu of a medical instrument.
Figure 2:
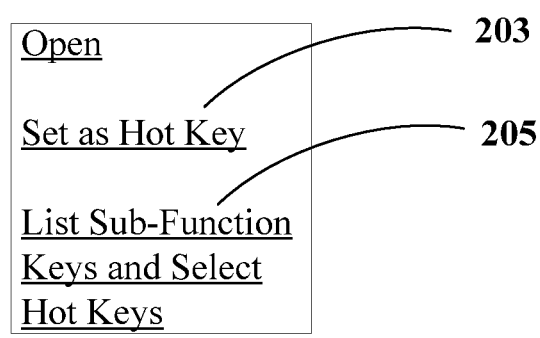
FIG. 2 is a schematic view of a hot key definition mode menu of a medical instrument.
Figure 3:
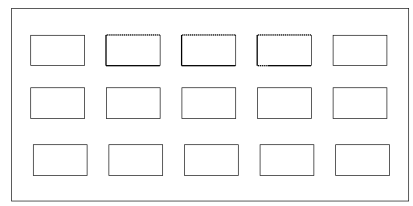
FIG. 3 is a schematic view of a hot key selection menu of a medical instrument.

One of the methods is shown in FIGS. 1, 2, and 3. FIG. 1 is a schematic view of a mode selection menu of a medical instrument according to an embodiment of the present disclosure. The mode selection menu is preset in an operation menu of the medical instrument, and multiple modes may be selected from the mode selection menu. For example, in this embodiment, the modes include a normal mode 101, a debugging mode 103, and a hot key definition mode 105. After selecting the hot key definition mode 105, the user further selects the function keys serving as the hot keys. The function keys may be selected in various ways. For example, a function key to which the cursor points is clicked, and a pop-up menu prompts the user that the function key can be defined as a hot key, shown as 203 in FIG. 2. If the function key is a hot key currently, the user is prompted whether to cancel the hot key; alternatively, if a sub-menu or sub-function keys appear after the function key is clicked, the user is prompted to directly select the desired hot keys or cancel the hot keys from the sub-menu or sub-function keys. The option of prompting the user to directly select the desired hot keys or cancel the hot keys from the sub-menu or sub-function keys is shown as 205 in FIG. 2. After the option is selected, the menu shown in FIG. 3 appears. After the user selects the option, highlighting, gray, or a blurred color may be used to indicate that the function key is set as a hot key currently.

Figure 4:
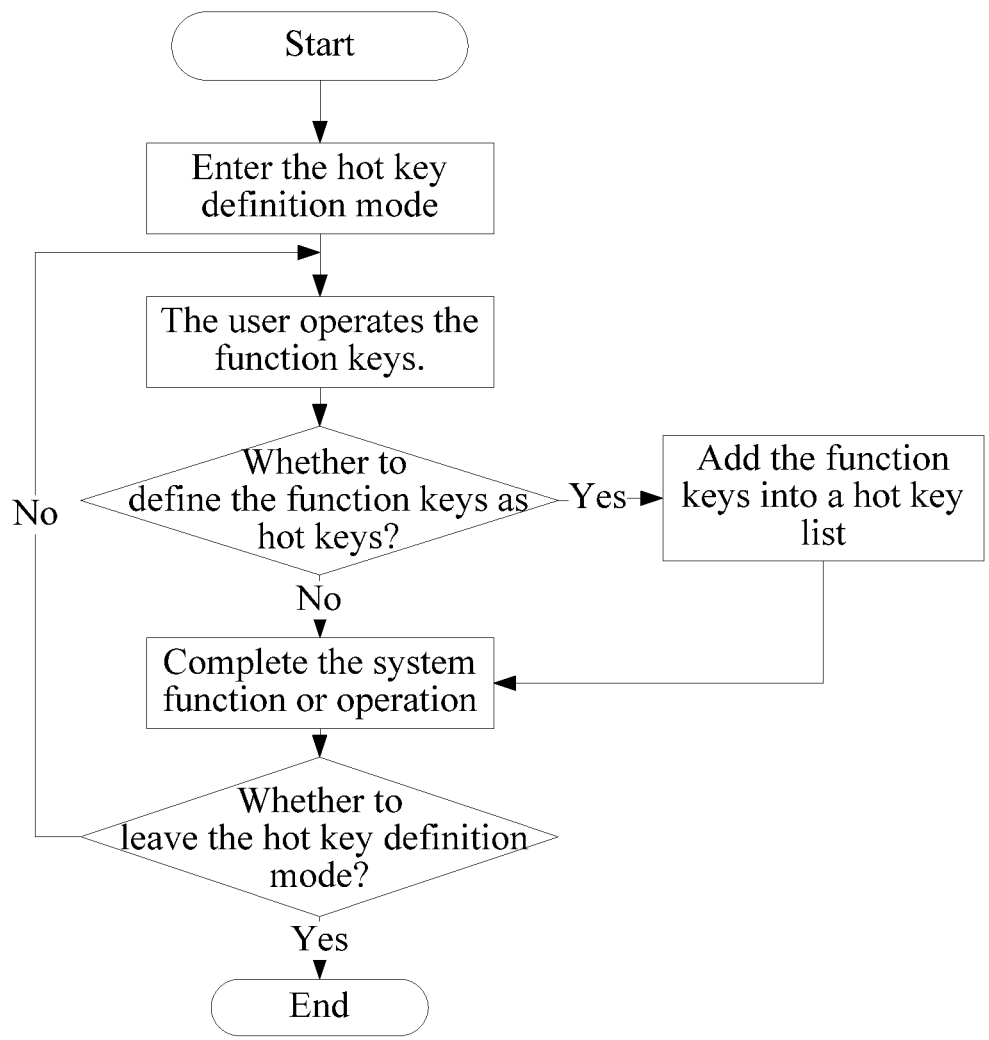
FIG. 4 is a flow chart of a method for using a medical instrument.

FIG. 4 is a flow chart of according to one embodiment. The embodiment is a special example, in which normal use is not influenced when the hot keys are defined.

Advantageously, when an operating system of the medical instrument is at a low level, and the operating device has only some simple hard keys, knobs, knobs with a key function, and/or a trackball, the simple operating device can be used to meet the requirements for defining the hot keys, which has a low cost and is easy to implement. For a medical instrument with an advanced operating system and a complicated operating device, the method is also applicable.

In another embodiment, when the cursor points to a function key, the user selects one function key. At this time, according to pre-settings of the system, the user can operate one of (or a combination of) the hard keys, so as to define the function key as a hot key. Alternatively, the user selects a hot key definition key displayed on the display interface to define the hot key, and, at this time, the cursor or focus remains on the function key serving as a hot key, and then the user operates the hot key definition key. When a touch screen is used, the hot key definition key may be clicked directly.

Advantageously, for a medical instrument with a small number of keys, the method is convenient in operation, especially when the user is very familiar with the medical instrument.

In other embodiments, when the user selects a function key, the function key generates a menu having an option for selecting and defining a hot key. After the option is selected, a signal for defining a hot key is generated. If the operating device is a mouse, the user right-clicks the function key, and a menu appears. The menu includes an option of selecting a hot key or canceling a hot key.

This method is similar to the first method, while the difference lies in that the step of entering the hot key definition mode is omitted, and the hot keys can be defined in use directly, so the operation is more convenient. Further, when the mouse is used, the method for defining hot keys is quite simple.

In still other embodiments, when the user operates some function keys much more frequently than other function keys, the frequently selected function keys may be considered more important than others, and the user needs to operate the function keys conveniently. Therefore, the function keys operated more frequently are automatically set as hot keys. The frequency may be the times that the function keys are clicked, a ratio of the times that the function keys are clicked to the total clicks of the user, or other values representing the frequency at which the user operates the function keys.

Generally, the function keys are bottom-layer ones for implementing specific functions, e.g., a function key for entering a parameter adjusting function. In one embodiment, the frequency statistics are performed only on this function key, and the function key is added as a hot key according to the statistical result. In some cases, the frequency statistics are also performed on normal menu function keys (that is, function keys that generate multiple sub-function keys after being selected), and the menu function keys may serve as hot keys after the frequency reaches a certain value.

In one embodiment, a lower threshold of the frequency is set. Once the frequency reaches the threshold, the function key is set as a hot key. The threshold is not necessarily set, and the function keys operated at higher frequencies are set as the hot keys.

Through this method, the function keys most commonly used by the user automatically serve as the hot keys, which reduce the operations of the user, and facilitate the operation on the commonly used function keys by the user.

In one embodiment, not only the frequency at which a function key is operated can be compared, but also a first function with the frequency as a variable can be set. The function keys serving as the hot keys are determined by comparing the value of the first function, e.g., several keys with the greatest values of the first function are selected as the hot keys, or the corresponding function key is selected as a hot key only when the value of the first function is the highest and is greater than a certain threshold at the same time. The first function includes, but is not limited to, the following:

$X=F*A$, where X is the value of the first function, F is the frequency, and A is a preset coefficient;

$X=F*A+B$, where X is the value of the first function, F is the frequency, and A and B are preset coefficients; and $X=F*F*A+B$, where X is the value of the first function, F is the frequency, and A and B are preset coefficients.

In practice, the importance of each function key may vary, and the necessity for setting each function key as a hot key may also vary. For example, though some function keys are operated frequently, the keys can be selected easily in one menu level. It is unnecessary to set these function keys as the hot keys. However, according to one embodiment, the function keys will be defined as the hot keys. In another aspect, some function keys can be selected only in multiple levels of the menus, and normally the function keys are less frequently used, for example, once a month, while in practice, the user needs to use the function keys for many times in a week. Since the frequency is still much lower than the frequencies at which other commonly used keys are selected, the function keys may not serve as the hot keys.

In order to solve the above problem or other similar problems, a preset first value may be set for each function key that may serve as a hot key. The value may be related to the importance of the function or whether the function key is easy to be selected. For example, for a function key that is easy to be selected and is less important, the value may be small, for example, 0.1; while for a function key that is difficult to be selected and is more important, the value may be great, for example, 0.5. A second function may be set for each function key. The second function may be related to the preset first value and the frequency at which the function key is selected. The second functions of the function keys may be the same or different, and the function keys serving as the hot keys are determined by comparing the second functions. For example, the second function may be $X=F*N$, where X is the value of the second function, F is the times that the function key is clicked, and N is the preset first value. The function keys with the greater calculated values of the second functions are selected as the hot keys, such that the hot keys generated automatically better meet the use habits of the user. The second function may be in other forms, e.g., $X=a*F*F*N+b*F*N+c$, where X is the value of the second function, F is the times that the function key is clicked, N is the preset first value, and a, b, and c are preset constants.

The above methods are mainly used to define the content of the hot keys. In addition, the arrangement and manner of displaying the hot keys may also be defined through the operating device. This may include, for example, positions for displaying the hot keys, e.g., the hot keys are preset to be displayed near four borders of the screen, and the user may select a position; arrangement of the hot keys, e.g., the hot keys are sorted by name or by use frequency; icon hot keys and character hot keys; and highlight hot keys, that is, the hot keys are displayed in a way different from normal, e.g., by using different colors, darkening, lighting, or blurred display, and additional background colors.

In one embodiment, the hot keys displayed on the display device may be displayed in a certain area, which is referred to as a hot key display area. Normally, the area has a fixed size, and the hot keys are displayed in the area. When the hot keys cannot be completely displayed, a special function key is provided, and other hot keys can be displayed after the user operates the special function key. The size and position of the hot key display area may be adjustable, e.g., the position and size may be adjusted through dragging a mouse, and at this time, the hot key display area may be considered a movable window. In one embodiment, the manner of displaying the hot keys, the hot key display area, or the border of the hot key display area may be adjusted, e.g., adjusted to blurred display, highlight display, or the like.

Currently, most medical instruments do not support a mouse and keyboard, have limited hardware capabilities, and are provided with a small display device. Accordingly, the hot key display area often cannot occupy a large area. Unfortunately, if the area is too small, it is inconvenient for the user to use the medical instrument. In order to solve this problem, in an embodiment of the present disclosure, the hot key display area is set to include at least two states, namely, a first state and a second state. In the first state, the hot keys are displayed in a first display area; while in the second state, the hot keys are displayed in a second display area. The first state and the second state are switchable. Generally, the size of the first display area is different from that of the second display area. When the medical instrument has much important information to be displayed, the state in which the hot key display area is small is used; and when the user intends to select the hot keys or there is not much important information to be displayed currently, the state in which the hot key display area is large is used.

Figure 5:
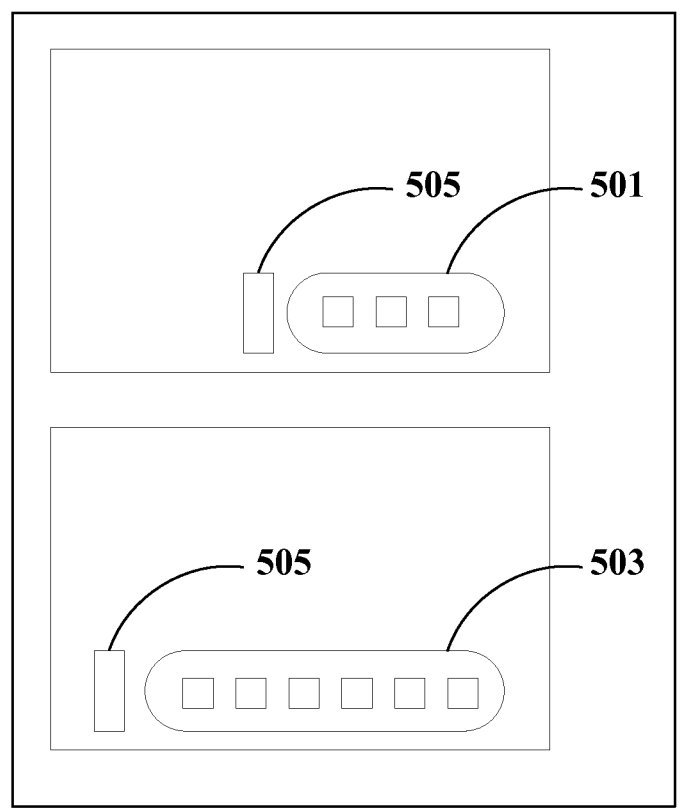
FIG. 5 is a schematic view of a hot key display area of a medical instrument.

The hot key display area having two states is taken for example in the following description. As shown in FIG. 5, in this embodiment, a first display area 501 corresponding to the first state is small, and fewer hot keys are displayed at this time; while a second display area 503 is large, and more hot keys are displayed at this time. The contents displayed in the first display area and the second display area may be partially the same, completely the same, or completely different.

Taking FIG. 5 for example, in the embodiment of the present disclosure, one or more of the following techniques are adopted to switch the states of the hot key display area.

A. The first state and the second state are switched after the user performs a preset operation on the operating device.

The preset operation is to operate a button displayed on the display device through the operating device, for example, a hot key state switching interface 505 shown in FIG. 5. The states are switched when the user operates the interface, for example, when the operating device is a knob with a button, the states are switched after the cursor is moved to 505 and the button is pressed. In addition, the preset operation may also be to operate a hardware button or key combination preset on an operation panel, and the first state and the second state are switched after the hardware button or key combination is operated.

B. The first state is a default state, and after the second state is entered and a first set time is reached, the first state is entered.

C. The first state is a default state, and after the second state is entered and the hot keys are not operated for a second set time, the first state is entered.

D. The first state is a default state, and after the second state is entered and the operating device is not operated for a third set time, the first state is entered.

E. The first state is a default state, and after the second state is entered and one of the hot keys is selected, the first state is entered.

F. The second state is a default state, and after the first state is entered and a fourth set time is reached, the second state is entered.

G. The second state is a default state, and after the first state is entered and the hot keys are not operated for a fifth set time, the second state is entered.

H. The second state is a default state, and after the first state is entered and the operating device is not operated for a sixth set time, the second state is entered.

I. The second state is a default state, and after the first state is entered and one of the hot keys is selected, the second state is entered.

J. When in the second state, if a preset trigger condition is generated, the first state is entered; the preset trigger condition includes alarm information to be displayed, important prompt information to be displayed, or other important information to be displayed. Generally, the display area of the medical instrument is limited, while a certain display area is needed when the trigger condition is generated. Therefore, the information is displayed in an area left blank after the second state is switched to the first state, that is, the display area of the information and the hot key display area are partially or completely reused. The information may be displayed partially in the area left blank, and partially in another area. When the alarm information, important prompt information, or other important information disappears, the second state is recovered automatically. Alternatively, the second state is recovered when a certain period of time is reached after the information disappears.

A hot key display area having two states in which the display areas are different is described in the above. In practice, the difference between the different display states may be different display contents. For example, a defibrillator monitor has different application modes, e.g., a monitor mode and a defibrillation mode, and the hot keys to be used in different modes are also different. Therefore, the first state is defined to display the hot keys for the monitor mode, and the second state is defined to display the hot keys for the defibrillation mode. The two states are set to be switchable, and the display areas of the two states may be the same or different. In summary, the hot keys may be displayed in different states, and the displayed hot keys are different in different states. In addition to the above methods, the method for switching between the first state and the second state further includes switching on receiving a signal for entering another application mode. That is, when the first state and the second state are corresponding to different application modes, for example, the monitor mode and the defibrillation mode, if the operator selects to enter one of the states having the hot keys, the display area is switched to the corresponding state automatically to display the corresponding hot keys. For example, if the operator selects to enter the defibrillation mode from the monitor mode, the display area is switched to the second state automatically to display the hot keys for the defibrillation mode.

A method for using a medical instrument is further provided in the present disclosure, which includes: receiving signals for defining hot keys, and defining the hot keys according to the signals.

The method for using a medical instrument includes at least one of the following circumstances.

Signals for selecting function keys serving as the hot keys or canceling function keys serving as the hot keys are received in a preset hot key definition mode, and the hot keys are defined according to the signals.

Alternatively or in addition, at least one predefined key is operated by a user to generate the signals for defining the hot keys, and the hot keys are defined according to the signals.

Alternatively or in addition, a menu is generated after an operator operates function keys, the menu has options for selecting and defining the hot keys, and the operator selects the options to generate the signals for defining the hot keys; the signals for defining the hot keys are received, and the hot keys are defined according to the signals.

Alternatively or in addition, statistics of a frequency that a user operates function keys are collected, the signals for defining the hot keys are generated when the operating frequency satisfies a preset condition, and the hot keys are defined according to the signals.

Alternatively or in addition, statistics of a frequency that a user operates function keys are collected, a preset first function is calculated according to the operating frequency, the signals for defining the hot keys are generated when the first function satisfies a preset condition, and the hot keys are defined according to the signals.

Alternatively or in addition, statistics of a frequency that a user operates function keys are collected, a preset second function is calculated according to the operating frequency and a preset first value of the function keys, the signals for defining the hot keys are generated when the second function satisfies a preset condition, and the hot keys are defined according to the signals.

Further, the hot keys are displayed in the hot key display area of the medical instrument, and the method for displaying the hot keys and the display area includes at least one of the following.

The hot keys may be displayed in a first state or a second state, the hot keys displayed in the first state are different from the hot keys displayed in the second state, and the first state and the second state are switchable.

Alternatively or in addition, the display device displays the hot key display area in a movable window.

Alternatively, or in addition the hot keys, the hot key display area, or a border of the hot key display area is displayed in a blurred or highlighted manner.

Further, when the hot keys are displayed in the first state or the second state, the first state and the second state are switched through at least one of the following modes.

The first state and the second state are switched after the user performs a preset operation on the operating device.

Alternatively or in addition, the first state is a default state, and after the second state is entered and a first set time is reached, the first state is entered.

Alternatively or in addition, the first state is a default state, and after the second state is entered and the hot keys are not operated for a second set time, the first state is entered.

Alternatively or in addition, the first state is a default state, and after the second state is entered and the operating device is not operated for a third set time, the first state is entered.

Alternatively or in addition, the first state is a default state, and after the second state is entered and one of the hot keys is selected, the first state is entered.

Alternatively or in addition, the second state is a default state, and after the first state is entered and a fourth set time is reached, the second state is entered.

Alternatively or in addition, the second state is a default state, and after the first state is entered and the hot keys are not operated for a fifth set time, the second state is entered.

Alternatively or in addition, the second state is a default state, and after the first state is entered and the operating device is not operated for a sixth set time, the second state is entered.

Alternatively or in addition, the second state is a default state, and after the first state is entered and one of the hot keys is selected, the second state is entered.

Alternatively or in addition, when in the second state, if a preset trigger condition is generated, the first state is entered; the preset trigger condition includes at least one of alarm information to be displayed, important prompt information to be displayed, other important information to be displayed, or reception of a signal for entering another application mode.

In the embodiments of the present disclosure, the hot keys are stored in a hot key list, and normally, the hot keys in the hot key list are stored in a certain sequence.

In the embodiments of the present disclosure, when the function keys are defined as the hot keys or the function keys serve as the hot keys, the keys are not necessarily displayed in the hot key display area directly. In one embodiment, the hot keys are added to the hot key list; as the hot key display area is limited and cannot display all the hot keys, after the hot keys are added to the list, if the current hot key display area has no space to display the hot keys, the hot keys are hidden, and the user can switch the hot keys in the hot key display area through the operating device to display the hot keys.

In one embodiment, switching method is as follows. A switching interface is disposed on at least one side of the left and right sides of the hot key display area, and after the switching interface is operated, the hot keys displayed in the hot key display area are switched according to the sequence of the hot keys in the list. In the embodiments of the present disclosure, the newly added hot key may be directly listed as a hot key displayed in the display area, or the newly added hot key is listed as a hot key displayed in the display area according to other preset conditions. For example, the preset condition may be a list of the importance of the function keys, and the function keys added as the hot keys are sorted automatically according to the list. If the importance of the newly added hot key is higher than the importance of all the current hot keys, the new hot key will be displayed at the first position automatically.

In the embodiments of the present disclosure, the user can operate the hot key list. For example, the user can set the sequence of displaying the hot keys. Normally, the first few hot keys are directly displayed in the hot key display area, and when the number of the hot keys exceeds the number of hot keys that can be displayed in the hot key display area, the later hot keys will be hidden. After the user performs a switching operation, the hidden hot keys will be displayed. Generally, the sequence switching is performed through the switching interface, or through other methods.

While specific embodiments and applications of various methods and systems for conducting experiments over the Internet have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer (or other electronic device). Alternatively, the steps may be performed by hardware components that contain specific logic for performing the steps, or by any combination of hardware, software, and/or firmware.

Embodiments of the present invention may also be provided as a computer program product including a machine-readable medium having stored thereon instructions that may be used to program a computer (or other electronic device) to perform processes described herein. The machine-readable medium may include, but is not limited to, floppy diskettes, optical disks, CD-ROMs, DVD-ROMs, ROMs, RAMs, EPROMs, EEPROMs, magnetic or optical cards, or other type of non-transitory media/machine-readable medium suitable for storing electronic instructions.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill in the art would further appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for using a medical instrument, comprising:
    receiving a user input selecting a function from a menu;
    tracking a frequency with which each function is selected from the menu, wherein the frequency is used for defining hot keys;
    associating the hot keys with functions according to the frequency with which each function is selected from the menu, by:
        determining a frequency value for each function in the menu by evaluating the expression X=F*N, where X is the frequency value for a function, F is the frequency that the function is selected, and N is a preset coefficient, wherein N is determined based on an importance of the respective function and a difficulty in selecting the respective function from the menu, wherein the importance of the respective function is independent of the frequency that the function is selected or other user input; and
        selecting the functions with the highest frequency values in the menu to associate with the hot keys; and
    displaying the hot keys in the hot key display area on a display device of the medical instrument.

2. The method of claim 1, wherein associating the hot keys with functions according to the frequency with which each function is selected from the menu further comprises:
    storing a threshold frequency value; and
    adding a function as a hot key in response to the frequency value exceeding the threshold frequency value.

3. The method of claim 2, wherein the threshold frequency value is based on a preset value, a number of hot keys available, or the frequency that the current hot keys are selected.

4. The method of claim 1 further comprising, determining a state in which to display the hot keys in the hot key display area, wherein the state defines a size of the hot key display area.

5. The method of claim 4, wherein determining the state is based on an operation performed by a user.

6. The method of claim 4, wherein determining the state is based on important information to be displayed on the display device of the medical instrument.

7. The method of claim 1, further comprising:
    storing a hot key list, wherein the defined hot keys are stored in a defined sequence in the hot key list;
    displaying a first portion of the hot key list in the hot key display area on the display device of the medical instrument in response to a first condition; and
    displaying a second portion of the hot key list in the hot key display area in response to a second condition.

8. A method for determining hot keys for display on a medical instrument, the method comprising:
    displaying a function menu on a display device of the medical instrument;
    receiving user input selecting functions from the function menu;
    storing frequency statistics to track a frequency with which each function is selected;
    determining a plurality of hot keys based on the frequency statistics, by:
        determining a frequency value for each function in the function menu by calculating a product of the frequency statistics for a function and a preset coefficient, wherein the preset coefficient for each function is determined based on an importance of the respective function and a difficulty in selecting the respective function from the function menu, wherein the importance of the respective function is independent of the frequency statistics or other user input;
        determining the plurality of hot keys by selecting the functions in the function menu with the highest frequency values; and
    displaying the hot keys in a hot key display area on the display device of the medical instrument.

9. The method of claim 8, wherein determining the plurality of hot keys further comprises:
    storing a threshold frequency value, wherein the threshold frequency value is based on a preset value, the number of hot key spaces available, or the frequency statistics; and
    adding a function as a hot key in response to the determined frequency value exceeding the threshold frequency value.

10. A medical instrument comprising:
    an input device configured to receive user input for operating the medical instrument;
    a processing device configured to perform functions selected by a user via the input device; and
    a display device configured to display results from the processing device, a menu for selecting a function to operate the medical instrument, and a plurality of hot keys in a hot key display area;
    wherein the processing device, to determine functions to associate with the plurality of hot keys in the hot key area, is further configured to:
        store frequency statistics to track a frequency that each function is selected;
        determine a frequency value for each function in the menu by evaluating an expression based on the frequency statistics and a preset coefficient, wherein the preset coefficient is based on an importance of the respective function and a difficulty in selecting the respective function from the menu, wherein the importance of the respective function is independent of the frequency statistics or other user input; and
        select the functions with the highest frequency values as the plurality of hot keys.

11. The medical instrument of claim 10, wherein the processing device is configured to determine a state in which to display the hot keys in the hot key display area of the display device, wherein the state defines a size of the hot key display area.

12. The medical instrument of claim 10, wherein the processing device is further configured to:
    store a hot key list, wherein the plurality of hot keys are stored in a defined sequence in the hot key list;

display a first portion of the hot key list in the hot key display area on the display device in response to a first condition; and display a second portion of the hot key list in the hot key display area on the display device in response to a second condition.

* * * * *